United States Patent
Allen

(10) Patent No.: US 11,045,184 B2
(45) Date of Patent: Jun. 29, 2021

(54) TISSUE ANCHOR, TISSUE ANCHOR ASSEMBLY, AND TISSUE ANCHOR SYSTEM

(71) Applicant: Coloplast A/S, Humlebaek (DK)

(72) Inventor: John J. Allen, Mendota Heights, MN (US)

(73) Assignee: Coloplast A/S, Humlebaek (DK)

( * ) Notice: Subject to any disclaimer, the term of this patent is extended or adjusted under 35 U.S.C. 154(b) by 173 days.

(21) Appl. No.: 16/296,293

(22) Filed: Mar. 8, 2019

(65) Prior Publication Data

US 2019/0274672 A1    Sep. 12, 2019

Related U.S. Application Data

(60) Provisional application No. 62/640,577, filed on Mar. 9, 2018.

(51) Int. Cl.
*A61B 17/04* (2006.01)
*A61B 17/06* (2006.01)
(Continued)

(52) U.S. Cl.
CPC .... *A61B 17/0401* (2013.01); *A61B 17/06066* (2013.01); *A61B 17/0487* (2013.01);
(Continued)

(58) Field of Classification Search
CPC ............ A61B 17/0401; A61B 17/0487; A61B 17/06019; A61B 17/06066; A61B 17/068; A61B 17/0682; A61B 17/0686; A61B 17/072; A61B 17/06057; A61B 17/07207; A61B 17/07292; A61B 17/076; A61B 17/08; A61B 17/083; A61B 17/085; A61B 17/10; A61B 17/105; A61B 2017/00805; A61B 2017/0403; A61B 2017/0409; A61B 2017/0412; A61B 2017/0414; A61B 2017/0416; A61B 2017/0427; A61B 2017/0429; A61B 2017/043; A61B 2017/0432; A61B 2017/0433; A61B 2017/0437; A61B 2017/044; A61B 2017/0464; A61B 2017/0496; A61B 2017/06057; A61B 2017/07214; A61B 2017/07221; A61B 2017/07228; A61B 2017/07235; A61B 2017/07242; A61B 2017/0725; A61B 2017/0727; A61B 2017/07264; A61B 2017/07271; A61B 2017/0728; A61B 2017/07285;
(Continued)

(56) References Cited

U.S. PATENT DOCUMENTS 6,506,190 B1    1/2003    Walshe
7,056,333 B2    6/2006    Walshe
(Continued)

FOREIGN PATENT DOCUMENTS

EP    3085336 A1    10/2016
WO    2009111802 A1    9/2009
(Continued)

*Primary Examiner* — Wade Miles
*Assistant Examiner* — Kankindi Rwego
(74) *Attorney, Agent, or Firm* — Coloplast Corp., Coloplast A/S; Nick Baumann

(57) ABSTRACT

A tissue anchor, tissue anchor assembly, and tissue anchor system is disclosed.

13 Claims, 14 Drawing Sheets

(51) Int. Cl.
*A61B 17/00* (2006.01)
*A61F 2/00* (2006.01)

(52) U.S. Cl.
CPC .............. *A61B 2017/00805* (2013.01); *A61B 2017/0403* (2013.01); *A61B 2017/044* (2013.01); *A61B 2017/0409* (2013.01); *A61B 2017/0412* (2013.01); *A61B 2017/0414* (2013.01); *A61B 2017/0416* (2013.01); *A61B 2017/0427* (2013.01); *A61B 2017/0464* (2013.01); *A61B 2017/0496* (2013.01); *A61B 2017/06057* (2013.01); *A61F 2/0045* (2013.01); *A61F 2220/0016* (2013.01)

(58) Field of Classification Search
CPC ...... A61F 2/0045; A61F 2/005; A61F 2/0054; A61F 2/0063; A61F 2002/0068; A61F 2002/0072; A61F 2220/0016
USPC .................................................. 606/151, 232
See application file for complete search history.

(56) References Cited

U.S. PATENT DOCUMENTS

| | | |
|---|---|---|
| 8,801,754 B2 | 8/2014 | Walshe |
| 9,827,083 B2 | 11/2017 | Allen et al. |
| 9,907,638 B2 | 3/2018 | Goldman et al. |
| 2009/0138042 A1 | 5/2009 | Thal |
| 2013/0217954 A1 | 8/2013 | Danna et al. |
| 2015/0157310 A1* | 6/2015 | Coillard-Lavirotte ...................... A61B 17/0401 606/232 |
| 2016/0038267 A1 | 2/2016 | Allen et al. |
| 2016/0338689 A1 | 11/2016 | Baird |
| 2018/0235746 A1* | 8/2018 | Pilgeram ............... A61F 2/0811 |

FOREIGN PATENT DOCUMENTS

| | | |
|---|---|---|
| WO | 2010065274 A1 | 6/2010 |
| WO | 2013114347 A1 | 8/2013 |
| WO | 2017011459 A1 | 1/2017 |

* cited by examiner

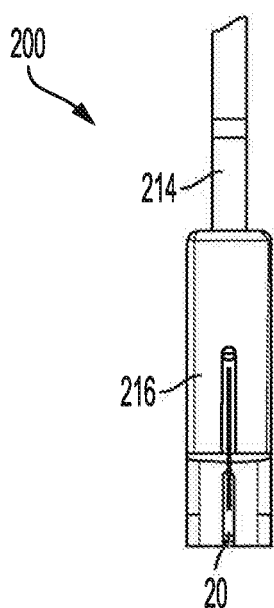
FIG. 13A
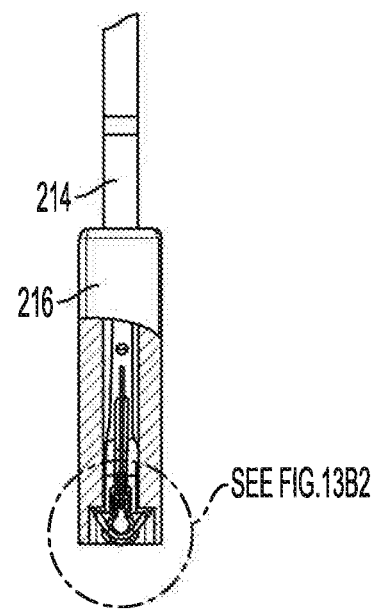
FIG. 13B1
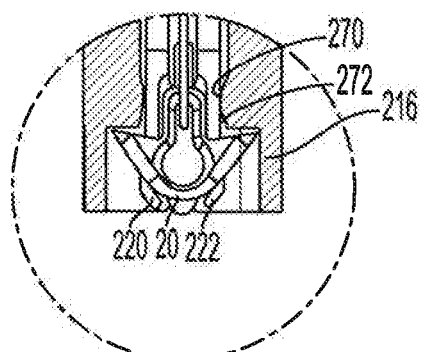
FIG. 13B2
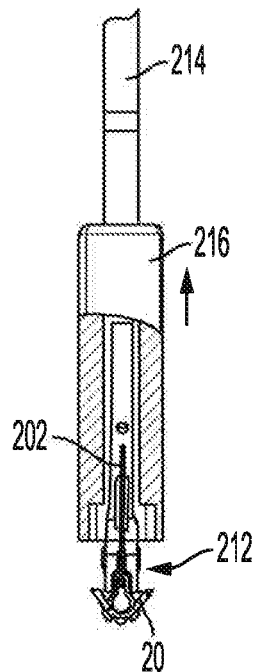
FIG. 13C
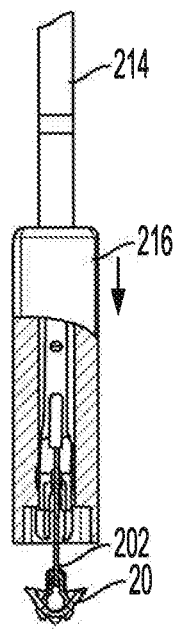
FIG. 13D

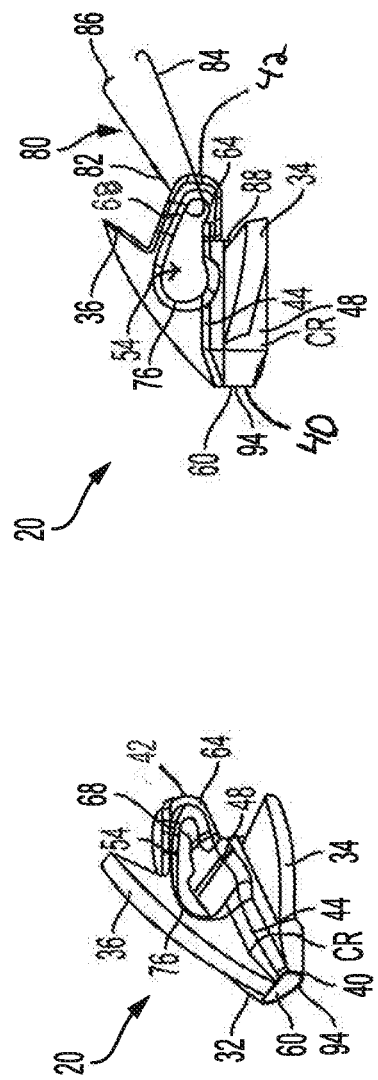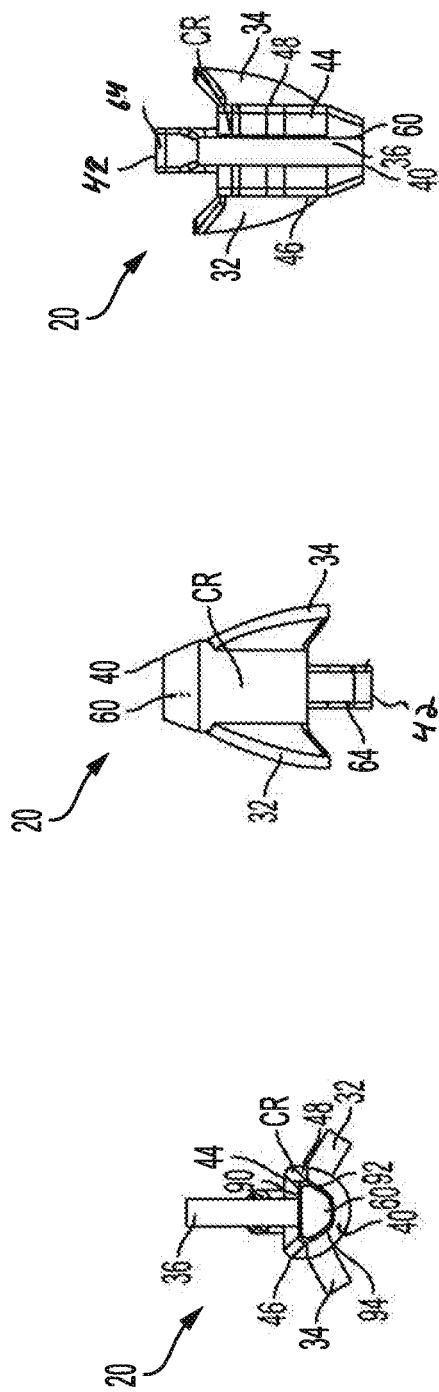

TISSUE ANCHOR, TISSUE ANCHOR ASSEMBLY, AND TISSUE ANCHOR SYSTEM

BACKGROUND

Treatment of pelvic organ prolapse includes placing some form of a support inside of the pelvis to support those organ(s) that have descended or moved away from their natural anatomic location. Often such a support is coupled to the sacrospinous ligament, as this ligament provides a durable and strong foundation. The sacrospinous ligament is usually accessed through a vagina incision, and the attachment of a support to the ligament presents a challenge to the surgeon in that the surgical instruments are manipulated within the confines of a relatively small space. In some cases, the surgeon digitally palpates a desired location for placement of a suture and is unable to see the suture site.

Improved suturing instruments and improved methods of delivering sutures would be welcomed by the surgical staff.

SUMMARY

One embodiment provides a tissue anchor including a leading-most end opposite of a trailing-most end, with a central longitudinal axis oriented from the leading-most end to the trailing-most end, with the leading-most end pointed and configured to penetrate tissue and the trailing-most end blunt; a front side opposite of a back side, with both of the front side and the back side of the tissue anchor being bi-laterally symmetric relative to the central longitudinal axis, with both of the front side and the back side of the tissue anchor including a central region centered on the central longitudinal axis, a first lateral region extending from the central region to a first barb, and a second lateral region extending opposite of the first lateral region from the central region to a second barb; an opening formed entirely through the front side and the back side and the central region of the tissue anchor, with the opening including a first aperture connected to a second aperture, with a diameter of the first aperture larger than a diameter of the second aperture by at least a factor of two, with the opening occupying more than 40% of a total area of the central region; a first slot formed longitudinally through an entirety of the first lateral region between the front side and the back side of the tissue anchor; and a second slot formed longitudinally through an entirety of the second lateral region between the front side and the back side of the tissue anchor. Advantages of the anchor include a large target hole for threading a suture combined with a minimally small total anchor size.

An aspect of the embodiment provides that a width of the tissue anchor, measured from an end of the first barb across the central region to an end of the second barb, is larger than a depth of the tissue anchor measured from the front side to the back side by at least a factor of three. The advantages of this configuration include an anchor having an excellent and substantially strong pull-out force with a thin, narrow thickness.

An aspect of the embodiment provides that an entirety of the first aperture is located between the leading-most end and the first barb. Advantages of this configuration provide a large target hole for threading a suture through the anchor while also providing a minimally sized and thin shank portion.

An aspect of the embodiment provides a pointed end of the first barb is located a longitudinal distance from the leading-most end of the tissue anchor, and an entirety of the first aperture is within the longitudinal distance. Advantages of this configuration provide a large target hole for threading a suture through the anchor without compromising the size of the anchor or having a thick shank with reduced pull-out force.

An aspect of the embodiment provides a distal portion of the tissue anchor includes the leading-most end and the first barb and the second barb, and a proximal portion of the tissue anchor includes a shank attached to the distal portion, with the second aperture formed in the shank and an entirety of the first aperture is formed in the distal portion of the tissue anchor. Advantages of this configuration provide a large target hole for threading a suture through the anchor without compromising the size of the anchor or having a thick shank with reduced pull-out force.

An aspect of the embodiment provides, for the case where a length of suture with a needle connected to the length of suture is provided, that the diameter of the first aperture is at least 3 times larger than a diameter of the needle. Advantages of this configuration provide a large target hole for threading the needle into the anchor while also having a small anchor with a high pull-out force provided by the wide-set barbs.

One embodiment provides a tissue anchor including a leading-most end opposite of a trailing-most end, with a central longitudinal axis oriented from the leading-most end to the trailing-most end, with the leading-most end pointed and configured to penetrate tissue and the trailing-most end blunt; a front side opposite of a back side, with both the front side and the back side of the tissue anchor including a central region centered on the central longitudinal axis, a first lateral region extending from the central region to a first tissue engaging arm, and a second lateral region extending opposite of the first lateral region from the central region to a second tissue engaging arm; a first slot formed longitudinally through an entirety of the first lateral region between the front side and the back side of the tissue anchor; and a second slot formed longitudinally through an entirety of the second lateral region between the front side and the back side of the tissue anchor; wherein, when viewed from the leading-most end along the central longitudinal axis, the first slot is a first rectangular opening formed in the first lateral region between the central region and a first lateral-most point of the first tissue engaging arm and the second slot is a second rectangular opening formed in the second lateral region between the central region and a second lateral-most point of the second tissue engaging arm, such that the first rectangular opening and the second rectangular opening combine to occupy about 20 percent of a total frontal area of the tissue anchor. Advantages of this configuration provide a lightweight and strong anchor in addition to a large target hole for threading the needle into the anchor while also having a small anchor with a high pull-out force provided by the wide-set barbs.

One embodiment provides a tissue anchor including a proximal portion providing a shank and a distal portion providing a tissue penetrating end; a front side opposite of a back side, with both the front side and the back side of the tissue anchor including a central region centered on a central longitudinal axis, a first lateral region extending from the central region to a first barb, and a second lateral region extending opposite of the first lateral region from the central region to a second barb; an opening formed entirely through the front side and the back side and the central region of the tissue anchor, with the opening including a first aperture connected to a second aperture, with an entirety of the first aperture formed within the distal portion and the second aperture formed in the shank; a first slot formed longitudinally through an entirety of the first lateral region between the front side and the back side of the tissue anchor; and a second slot formed longitudinally through an entirety of the second lateral region between the front side and the back side of the tissue anchor. The opening is separated from the first slot and the second slot by a wall. Advantages of this configuration provide a lightweight and strong anchor in addition to a large target hole for threading the needle into the anchor while also having a small anchor with a high pull-out force provided by the wide-set barbs.

One embodiment provides a tissue anchor including a shank connected to a tissue penetrating head, with the shank providing a proximal most end of the tissue anchor and the tissue penetrating head providing a tissue penetrating leading end of the tissue anchor; where the tissue penetrating head extends in a longitudinal direction from the tissue penetrating leading end to the shank; an opening formed in the tissue anchor orthogonal to the longitudinal direction, with the opening including a first aperture connected to a second aperture, with an entirety of the first aperture formed through a thickness of the tissue penetrating head and the second aperture formed through a thickness of the shank; where the tissue penetrating head includes a first lateral region extending from the first aperture to a first barb and a second lateral region extending opposite of the first lateral region from the first aperture to a second barb, with a first slot formed longitudinally through an entirety of the first lateral region of the tissue penetrating head and a second slot formed longitudinally through an entirety of the second lateral region of the tissue penetrating head. The first aperture is separated from the first slot and the second slot by a wall. Advantages of this configuration provide a lightweight and strong anchor in addition to a large target hole for threading the needle into the anchor while also having a small anchor with a high pull-out force provided by the wide-set barbs.

One embodiment provides a tissue anchor assembly including a tissue anchor including a body having an aperture and a pointed end configured for tissue penetration; a length of suture looped through the aperture of the tissue anchor and having a first suture section extending away from a front side of the tissue anchor and a second suture section extending away from a back side of the tissue anchor; and an adjustable anchor including a sleeve placed over a central shaft, with the sleeve having a single proximal hole formed through the sleeve, a first distal hole formed through the sleeve, and a second distal hole formed through the sleeve, with the single proximal hole located between opposing lateral edges of the sleeve and placed laterally between the first distal hole and the second distal hole. The first suture section and the second suture section are each inserted into the single proximal hole formed in the sleeve and retained between the sleeve and the central shaft, with the first suture section exiting the sleeve through the first distal hole and the second suture section exiting the sleeve through the second distal hole. Advantages of this configuration provide an adjustable button useful for adjusting tension in the suture between the anchor and the button.

One aspect of the embodiment provides, where the central shaft includes splines extending in a radial direction away from the central shaft, that the first suture section and the second suture section are each engaged between the splines of the central shaft and the sleeve. Advantages of this aspect is that the button provides for tensioning and loosening the suture and the tension between the button and the anchor.

One embodiment provides a tissue anchor system including a tissue anchor comprising: a leading-most end opposite of a trailing-most end, with a central longitudinal axis oriented from the leading-most end to the trailing-most end, with the leading-most end pointed and configured to penetrate tissue and the trailing-most end blunt, a front side opposite of a back side, with both of the front side and the back side of the tissue anchor being bi-laterally symmetric relative to the central longitudinal axis, with both of the front side and the back side of the tissue anchor including a central region centered on the central longitudinal axis, a first lateral region extending from the central region to a first tissue engaging arm, and a second lateral region extending opposite of the first lateral region from the central region to a second tissue engaging arm, an opening formed entirely through the front side and the back side and the central region of the tissue anchor, with the opening including a first aperture connected to a second aperture, with a diameter of the first aperture larger than a diameter of the second aperture by at least a factor of two, with the opening occupying more than 40% of a total area of the central region; a first slot formed longitudinally through an entirety of the first lateral region between the front side and the back side of the tissue anchor, and a second slot formed longitudinally through an entirety of the second lateral region between the front side and the back side of the tissue anchor; a length of suture looped through the opening of the tissue anchor and having a first suture section extending away from a front side of the tissue anchor and a second suture section extending away from a back side of the tissue anchor; and a tool configured to place the tissue anchor into tissue, the tool comprising a clip having a first clip arm insertable into the first slot of the tissue anchor and a second clip arm insertable into the second slot of the tissue anchor. The first clip arm and the second clip arm engage with a wall that forms the first aperture of the tissue anchor to retain the tissue anchor relative to the tool, and the the first clip arm and the second clip arm move laterally to disengage with the wall that forms the first aperture of the tissue anchor to eject the tissue anchor from the tool. Advantages include protection of a retained anchor until the anchor is delivered out from the tool.

An aspect of the embodiment provides an adjustable anchor coupled to the first suture section and the second suture section. The advantage of this aspect is to provide a delivery mechanism and tensioning mechanism to the suture as provided by the button and the anchor.

Another embodiment provides a tissue anchor comprising a front side opposite of a backside, a central region between the front side and the backside; a first barb and a second barb extending laterally from opposing sides of the central region; a third barb extending from a top surface of the central region angled relative to at least one of the first barb and the second barb; a slot arranged through the central region from the front side to the backside configured to interface with a delivery tool; and an aperture arranged vertically offset from the slot and with at least a portion of the aperture arranged distal to the slot, the aperture being configured to allow passage of a suture therethrough. Advantages of this embodiment include a plurality of barbs to engage tissue and an aperture having a size that allows the surgeon to insert other suture lines through the anchor.

One aspect of the embodiment includes the aperture having a first portion and a second portion with the first portion and the second portion of the aperture being of different sizes. One aperture allows for easy threading of the suture and the other aperture engages the suture when force is applied to the suture. Embodiments include where first portion of the aperture is smaller than the second portion of the aperture. Embodiments include where the aperture increases in size toward the leading-most end of the anchor; and where the aperture extends longitudinally distal to the third barb.

One aspect of the embodiment includes where a distal end of the slot is offset from the aperture to facilitate interaction with the delivery tool.

Aspects of the embodiment include where the first barb and the second barb extend at a downward angle relative to the opposing side surfaces of the central region; where the slot includes an upper surface extending perpendicularly laterally across the central region; where the upper surface of the slot is substantially flat and a lower surface of the slot is curved; and where the lower surface of the slot is a semi-circle.

Another embodiment includes a tissue anchor system comprising a tissue anchor including a front side opposite of a backside, a central region between the front side and the backside, a first barb and a second barb extend laterally from opposing sides of the central region, a third barb extending from a top surface of the central region and perpendicular to at least one of the first barb and the second barb, a slot arranged through the central region from the front side to the backside, an aperture arranged vertically offset from the slot and with at least a portion of the aperture arranged distal to the slot, the aperture being configured to allow passage of a suture therethrough; and a tool configured to place the tissue anchor into tissue, the tool including a handle portion, a shaft extending from the handle portion, a cannula extending from a distal end of the shaft configured to extend through the slot in the anchor, and a plunger button arranged with the handle portion and configured to actuate the cannula in response to an applied force. Advantages of the embodiment include secure handling of the anchor by the tool, particularly where the tool is inserted through a body incision and along other tissue prior to placing the anchor in the targeted tissue. Aspects provide for the shaft having a groove into which the anchor nests.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 13A as a top view of the tool illustrating the sleeve enclosing an anchor captured by the clip of the shaft.

FIG. 13B1 illustrates the anchor captured by the clip of the shaft, and FIG. 13B2 is an expanded view showing the anchor captured by the clip of the shaft.

FIG. 13C as a top view of the shaft moved axially passed the sleeve to a position for deployment of the anchor.

FIG. 13D as a top view of the anchor deployed out of the tool.

FIG. 14 is a perspective view of one embodiment of an anchor.

FIG. 15 is a side view of the anchor illustrated in FIG. 14.

FIG. 16 is a front view of the anchor illustrated in FIGS. 14-15.

FIG. 17 is a bottom view of the anchor illustrated in FIGS. 14-16.

FIG. 18 is a top view of the anchor illustrated in FIGS. 14-17.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Tissue includes soft tissue, which includes dermal tissue, sub-dermal tissue, ligaments, tendons, periosteum, or membranes. As employed in this specification, the term "tissue" does not include bone.

In this specification, end means endmost and end portion means that segment that is adjacent to and extends from the end. For example, a proximal end is that end location of a handheld instrument that is nearest a user, and a proximal end portion is that segment (e.g., a handle of the handheld instrument) that is adjacent to and extends distally away from the proximal end.

Figure 1:
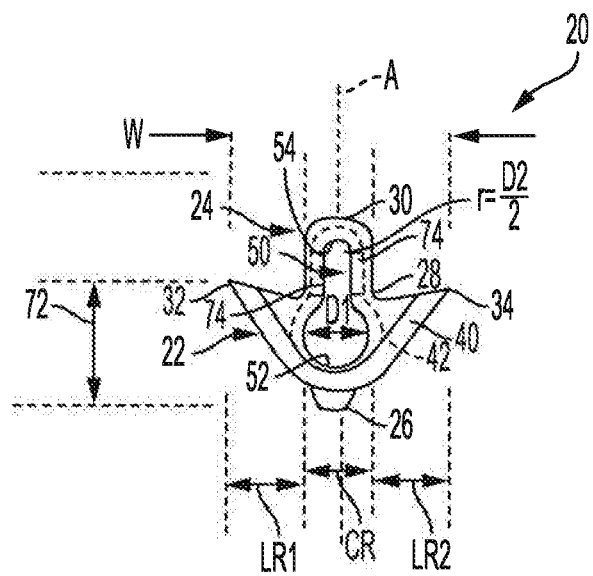
FIG. 1 is a top view of a front side of one embodiment of an anchor.
Figure 2:
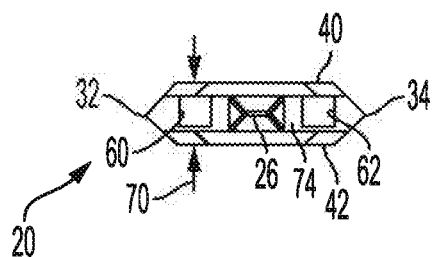
FIG. 2 is a front view of one embodiment of a distal end of the anchor illustrated in FIG. 1.

FIG. 1 is a top view and FIG. 2 is a front view of a distal end of one embodiment of a tissue anchor 20. The tissue anchor 20 includes a distal portion 22 and a proximal portion 24. The distal portion 22 provides a leading-most end 26 and the proximal portion 24 includes a shank 28 that terminates in a trailing-most end 30. A central longitudinal axis A is oriented from the leading-most end 26 to the trailing-most end 30. In one embodiment, the leading-most end 26 is pointed and configured to penetrate tissue and the trailing-most end 30 is blunt. When the anchor 20 is handled by the surgical staff, the surgeon is nearest to the trailing most end 30 and farthest from the leading-most end 26, which is consistent with the usual convention that the surgeon is nearest to the proximal portion of a device.

The tissue anchor 20 includes a front side 40 opposite of a backside 42. The front side 40 (top face) and the back side 40 (bottom face) can have different conformations. In one embodiment, each of the front side 40 and the backside 42 is configured to be bi-laterally symmetric relative to the central longitudinal axis A. Bi-laterally symmetric means the left lateral side has the same conformation as the right lateral side, which is to say that the two lateral sides are mirror images of each other. The front side 40 and the backside 42 of the tissue anchor include a central region CR that is centered on the longitudinal axis A, a first lateral region LR1 extending from the central region CR to a first barb 32, and a second lateral region LR2 extending opposite from the first lateral region LR1 from the central region CR to a second barb 34. In one embodiment, the leading-most end 26 is pointed in the form of a conical projection that is attached between the first lateral region LR1 and the second lateral region LR2, where the first lateral region LR1 and the second lateral region LR2 are arched in a parabola-shape and support the conical projection of the leading-most end 26.

In one embodiment, an opening 50 is formed entirely through the tissue anchor 20 from the front side 40 through the backside 42 in the central region CR. The opening 50 includes a first aperture 52 connected to a second aperture 54, with a diameter D1 of the first aperture 52 sized to be larger than a diameter D to of the second aperture 54 by at least a factor of 2. FIG. 1 illustrates one exemplary embodiment where a radius r of the second aperture 54 is equal to the diameter D2/2, although other ratios are possible. In one embodiment, the opening 50 occupies more than 40% of a total area of the central region CR.

FIG. 2 is a front view of the tissue anchor 20. FIG. 2 shows the total frontal area of the anchor. A first slot 60 is formed longitudinally through an entirety of the first lateral region LR1 between the front side 40 and the backside 42. A second slot 62 is formed longitudinally through an entirety of the second lateral region LR2 between the front side 40 and the backside 42 of the tissue anchor 20.

When the tissue anchor 20 is viewed from the leading-most end 26 along the central longitudinal axis A, the first slot 60 is a first rectangular opening formed in the first lateral region LR1 between the central region CR and the first barb 32, and the second slot 62 is formed as a second rectangular opening formed in the second lateral region LR2 between the central region CR and the second barb 34. In one embodiment, the first rectangular opening formed by the first slot 60 and the second rectangular opening formed by the second slot 62 combine to occupy about 20% of a total frontal area of the tissue anchor 20.

In one embodiment, a width W of the tissue anchor 20 measured from an end of the first barb 32 across the central region CR to an end of the second barb 34 is larger than a depth 70 of the tissue anchor measured from the front side 40 to the backside 42 by at least a factor of 3.

The first aperture 52 is larger than the second aperture 54 and configured to allow the surgical staff to easily thread a length of suture into the opening 50. In one embodiment, an entirety of the first aperture 52 is located between the leading-most end 26 and the end of the first barb 32. In one embodiment, at least 50% of the first aperture 52 is located between the leading-most end 26 and the end of the first barb 32.

In one embodiment, a pointed end of the first barb 32 is located a longitudinal distance 72 from the leading-most end 26 of the tissue anchor 20, and an entirety of the first aperture 50 is formed within the longitudinal distance 72.

In one embodiment, the distal portion 22 of the tissue anchor 20 includes the leading-most end 26 and the first barb 32 and the second barb 34; and the proximal portion 24 of the tissue anchor 20 includes the shank 28 that is attached to the distal portion 22, and the second aperture 54 is formed in the shank 28 and an entirety of the first aperture 52 is formed in the distal portion 22.

In one embodiment, the proximal portion 24 provides the shank 28 and the distal portion 22 provides the tissue penetrating end 26, and the opening 50 is formed entirely through the front side 40 and the back side 42 and the central region CR of the tissue anchor 20, with the opening 50 including the first aperture 52 connected to the second aperture 54, with an entirety of the first aperture 52 formed within the distal portion 22 and the second aperture 54 formed in the shank 28. The first slot 60 is formed longitudinally through an entirety of the first lateral region LR1 between the front side 40 and the back side 42 of the tissue anchor 20, and the second slot 62 is formed longitudinally through an entirety of the second lateral region LR2 between the front side 40 and the back side 42 of the tissue anchor 20. The opening is separated from the first slot 60 and the second slot 62 by a wall 74. In one embodiment, the shank 28 is connected to a tissue penetrating head defined by the distal portion 22, with the shank 28 providing the proximal most end 30 of the tissue anchor 20 and the tissue penetrating head providing the tissue penetrating leading end 26 of the tissue anchor 20. The tissue penetrating head extends in a longitudinal direction from the tissue penetrating leading end 26 to the shank 28. The opening 50 is formed in the tissue anchor 20 orthogonal to the longitudinal direction, with the opening 50 including the first aperture 52 connected to the second aperture 54, with an entirety of the first aperture 52 formed through a thickness of the tissue penetrating head and the second aperture 54 formed through a thickness of the shank 28. The tissue penetrating head includes the first lateral region LR1 extending from the first aperture 52 to the first barb 32 and the second lateral region LR2 extending opposite of the first lateral region LR1 from the first aperture 52 to a second barb 34. The first slot 60 is formed longitudinally through an entirety of the first lateral region LR1 of the tissue penetrating head and the second slot 62 is formed longitudinally through an entirety of the second lateral region LR2 of the tissue penetrating head. The first aperture 52 is separated from the first slot 60 and the second slot 62 by the wall 74. In a top plan view of the front side 40 of the tissue anchor 20, the opening 50 occupies from about 20% to 30% of the total planar area of the tissue anchor 20. In a front plan view of the leading-most end 26 of the tissue anchor 20, the first and second slots occupy from about 6% to 10% of the frontal area of the tissue anchor 20.

The tissue anchor 20 is suitably formed from a polymer that is not bioabsorbable, or a polymer that is bioabsorbable, or from a metal. In one embodiment, the tissue anchor 20 is not bioabsorbable and is formed from one of polypropylene, polyethylene, or a polyether ether ketone. In one embodiment, the tissue anchor 28 is resorbable after implantation into the tissue and is formed from, as examples, poly(L-lactic acid), poly(glycolic acid), poly(ortho ester), or poly(epsilon-caprolactone). In one embodiment, the tissue anchor 20 is metal and is formed from, as examples, stainless steel or titanium.

Figure 3:
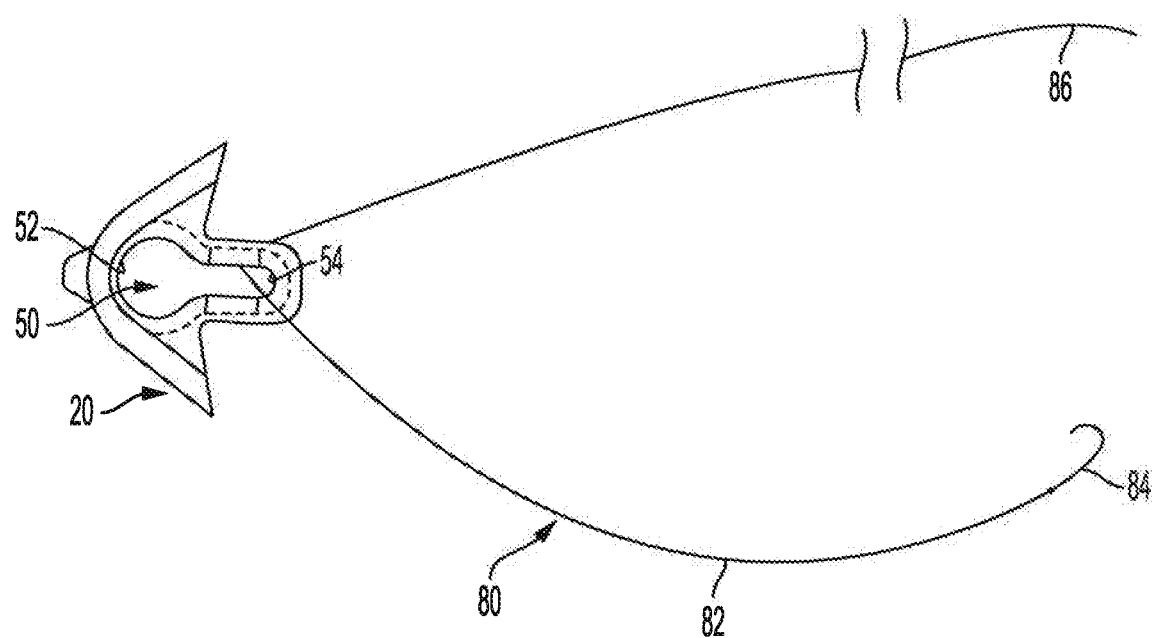
FIG. 3 is a top view of one embodiment of the anchor illustrated in FIG. 1 coupled to a double-armed suture.

FIG. 3 is a top view of one embodiment of the tissue anchor 20 coupled with a double-armed suture 80. The double-armed suture 80 includes a length of suture 82 having a first needle 84 connected to a first end of the suture 82 and a second needle 86 connected to a second end of the suture 82. The first needle 84 is fish-hook shaped, and the second needle 86 is not fish-hook shaped. Surgeons often have a strong preference for the type of suture and the size of the needles provided by the double-armed suture 80. The surgeon may desire to couple the double-armed suture 82 to an anchor for use in treating pelvic organ prolapse. The typical anchor includes a tissue penetrating portion at the front end and a shank at the proximal end, where the shank includes a small eyelet. Surgeons have expressed a level of frustration when passing one of the needles of the double-armed suture through the usual small eyelet of a typical anchor. The anchor 20 provides an opening 50 having the first aperture 52 sized to be significantly larger than the second aperture 54, such that the first aperture 52 provides a large target opening for passing one of the needles 84, 86 through the anchor 20. In one embodiment, the diameter D1 of the first aperture 52 is in a range from 1-3 times larger than a diameter of the needle 84 or a diameter of the needle 86, and preferably in a range from 1-1.5 times larger than a diameter of the needle 84 or a diameter of the needle 86. Consequently, passage of the double-armed suture 80 through the opening 50 of the anchor 20 is substantially easier and more convenient than passing a double-armed suture through a conventional eyelet of a conventional anchor.

The opening 50 extends most of the length of the tissue anchor 20. In one embodiment, the opening 50 extends in a range from 60% to 80% of the length of the anchor 20. The opening 50 extends substantially into the anchor head or distal region 22, which stands in stark contrast to the typical tissue anchor. The configuration of the relative diameters of the first aperture 52 compared to the second aperture 54 adapts the suture 82 to be transferred into the second aperture 54 when tension is applied to the suture. Thus, although the opening 50 is a substantial portion of the length of the anchor 20, the anchor 20 is still stable when deployed due to the self-aligning nature of the second aperture 54 relative to the large target hole of the first aperture 52.

The anchor 20 allows passage of the surgeon's choice of a prepackaged, double-armed suture. The first aperture 52 has a diameter D1 of at least 1.0 mm and preferably the diameter D1 of the first aperture 52 is at least 1.5 mm to accommodate a wide variety of needle sizes and shapes that are commercially available with USP Size 0 sutures.

Anchors for securement of a suture in soft tissue have two features that influence its design: a barb feature that resists pull-out from tissue and an attachment feature (an eyelet) for retaining a suture. The distance or spacing from the wall of the anchor shank to the tip of the barb is related to pull-out strength, and the pull-out strength of the barb generally increases with the spacing.

For anchoring in soft tissue, it is desirable to minimize the overall size of the anchor while still retaining the tissue-anchoring features.

Some surgeons prefer to use a double-armed suture where needles are attached at both ends. However, conventional anchors having a conventional eyelet present a challenge because the anchor eyelet is too small to pass a needle. Thus, the surgical staff is instructed to attach the second needle to the suture after threading the suture through the small eyelet. Consequently, the choice of needle type and suture type is limited to use with anchors that the anchor manufacturer is willing to produce. A physician may also thread the second needle during the procedure, but this can be a tedious task and the needle itself may not be ideal for the suturing steps.

The anchor 20 allows passage of the surgeon's choice of pre-packaged, double-armed suture. The first aperture 52 is sized to accommodate the wide variety of needle sizes and shapes that are commercially available with USP Size 0 sutures. While it is possible to increase the size of the existing eyelet in a conventional anchor, this would leave a thin wall in the shank, resulting in a weakened part. Increasing the width of the shank is possible, but this approach results in enlargement of the head of the anchor to maintain the spacing to achieve the desired pull-out strength. Consequently, increasing the size of the existing eyelet in a conventional anchor would result in a larger anchor that is less desirable.

The anchor 20 is a better solution since the eyelet (opening 50) is shaped to accommodate needles. The first aperture 52 has a relatively large diameter of, in one example, of 1.5 mm which is large enough for needles that are pre-attached to commercially available sutures. The first aperture 52 is distal to the barbs 32, 34 and is located within an area of the head of the anchor, so there is no increase in the size of the shaft 28 or the anchor 20. In fact, the overall size of the anchor 20 is significantly less than the currently available soft tissue anchors.

Figure 4A:
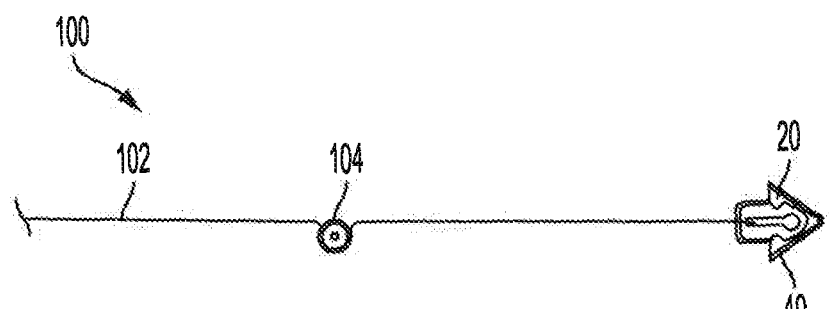
FIG. 4A as a side view of one embodiment of an anchor assembly.
Figure 4B:
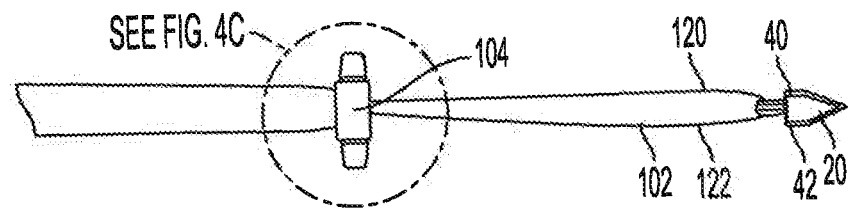
FIG. 4B is a top view of the anchor assembly illustrated in FIG. 4A.
Figure 4C:
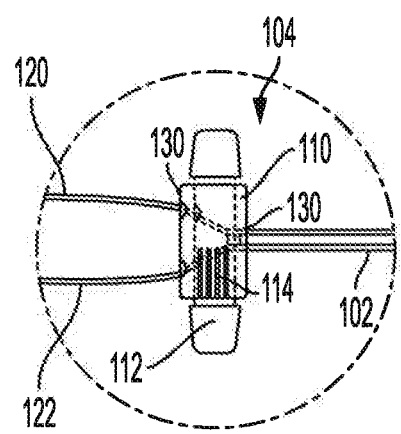
FIG. 4C is a detailed view of a button of the anchor assembly illustrated in FIG. 4A.

FIG. 4A is a side view, FIG. 4B as a top view, and FIG. 4C is an expanded view of a tissue anchor assembly 100. The tissue anchor assembly 100 includes a suture 102 coupled between the tissue anchor 20 and a button 104. The tissue anchor 20 is provided for anchoring the tissue anchor assembly 100 into soft tissue, and the button 104 is provided to allow adjustment of the tension within the suture 102.

FIG. 4C is an expanded view of the button 104. The button 104 includes a sleeve 110 disposed over a central shaft 112, where one of the sleeve 110 or the shaft 112 is provided with locking splines 114.

The suture 102 includes a first suture section 120 extending away from a front side 40 of the tissue anchor 20 and a second suture section 122 extending away from a backside 42 of the tissue anchor 20.

In one embodiment, the sleeve 110 includes a single proximal hole 130, a first distal hole 132, and a second distal hole 134, with the single proximal hole 130 located between opposing lateral edges of the sleeve 110 and placed laterally between the first distal hole 132 and the second distal hole 134.

In one embodiment, the locking splines 114 engage with the second suture section 122 to effectively connect the button 104 to the second suture section 122. Consequently, when tension is applied to the second suture section 122, the button 104 is engaged with the second suture section 122 and moves in the direction of the applied tension to loosen the tissue anchor assembly 100. In other words, tension applied to the second suture section 122 displaces the button 104 and increases a distance between the button 104 and the tissue anchor 20.

In one embodiment, tension applied to the first suture section 120 applies tension through the tissue anchor 20 and causes the button 104 to move in a direction towards a tissue anchor 20. Consequently, tension applied to the first suture section 120 reduces a distance between the button 104 and the tissue anchor 22 effectively "tighten" the tissue anchor assembly 100.

In one embodiment, the tissue anchor assembly includes the soft tissue anchor 20 and the button 104 which operates as an adjustable anchor provided to adjust tension in the suture 102.

Figure 5:
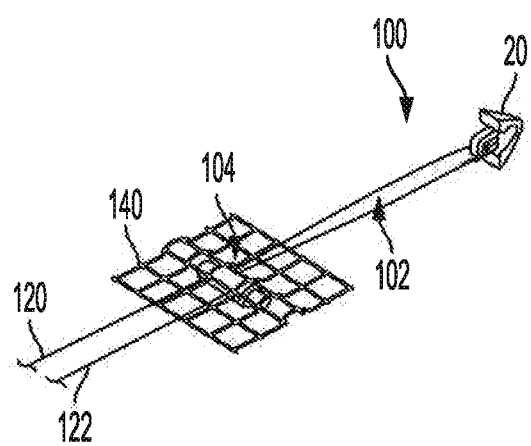
FIG. 5 is a perspective view of the anchor assembly illustrated in FIG. 4A coupled to a support material.

FIG. 5 is a perspective view of the tissue anchor assembly 100 coupled to a support 140. In one embodiment, the button 104 has a relatively large aspect ratio where a length of the button is larger than a diameter of the button. The large aspect ratio of the button 104 allows one end of the button to be pushed through the support 140 to capture the button on a bottom side of the support while the suture 102 in the tissue anchor 20 remains on a top side of the support 140.

In one embodiment, the surgeon will place the soft tissue anchor 20 into soft tissue such as the sacrospinous ligament and then subsequently couple the button 104 to a support material 140. Tension applied to the first suture section 120 operates to tighten the tissue anchor assembly 100 and draw the support 140 closer to the tissue anchor 20. If the surgeon desires, tension applied to the second suture section 122 will loosen the tissue anchor assembly 100 and move the support 140 away from the soft tissue anchor 20.

The support 140 can be a synthetic support, a native tissue support, a human tissue support harvested from a cadaver, or a tissue support harvested from a transgenic animal such as a porcine animal. In one embodiment, the support 140 is a Restorelle® synthetic mesh material available from Coloplast Corp., Minneapolis Minn.

A tissue anchor system 200 is provided that includes the tissue anchor 20, a length of suture 202, and a tool 204 to place the tissue anchor 20 into soft tissue. One embodiment of the tissue anchor system 200 is best illustrated in FIG. 13A, which is described below.

Figure 6:
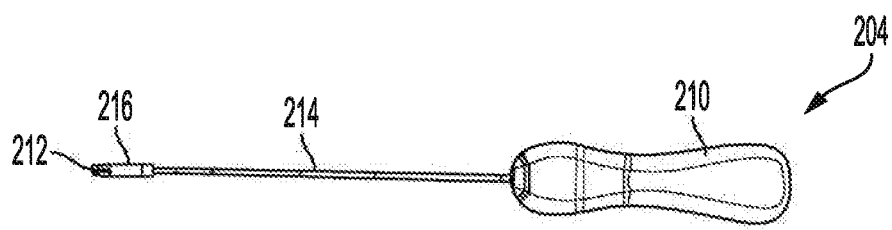
FIG. 6 is a top view.
Figure 7:
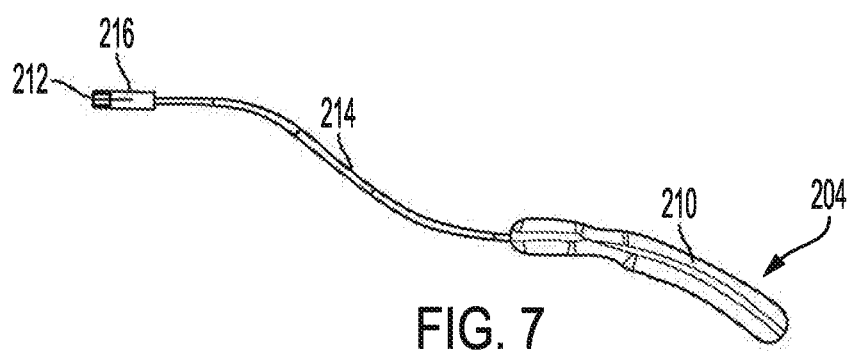
FIG. 7 is a side view.
Figure 8:
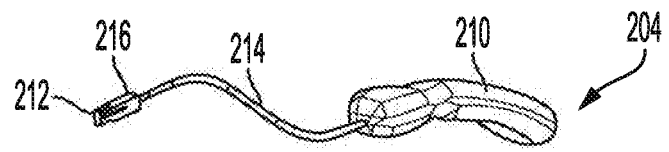
FIG. 8 is a perspective view of one embodiment of a tool for placing the anchor illustrated in FIG. 1.

FIG. 6 is a top view, FIG. 7 is a side view, and FIG. 8 is a perspective view of one embodiment of the tool 204. The tool 204 includes a handle 210 on a proximal end, a clip 212 on a distal end, a shaft 214 coupled between the handle 210 and the clip 212, and a sleeve 216 that is provided to protect the clip 212 when it is engaged with the anchor 20.

Figure 9:
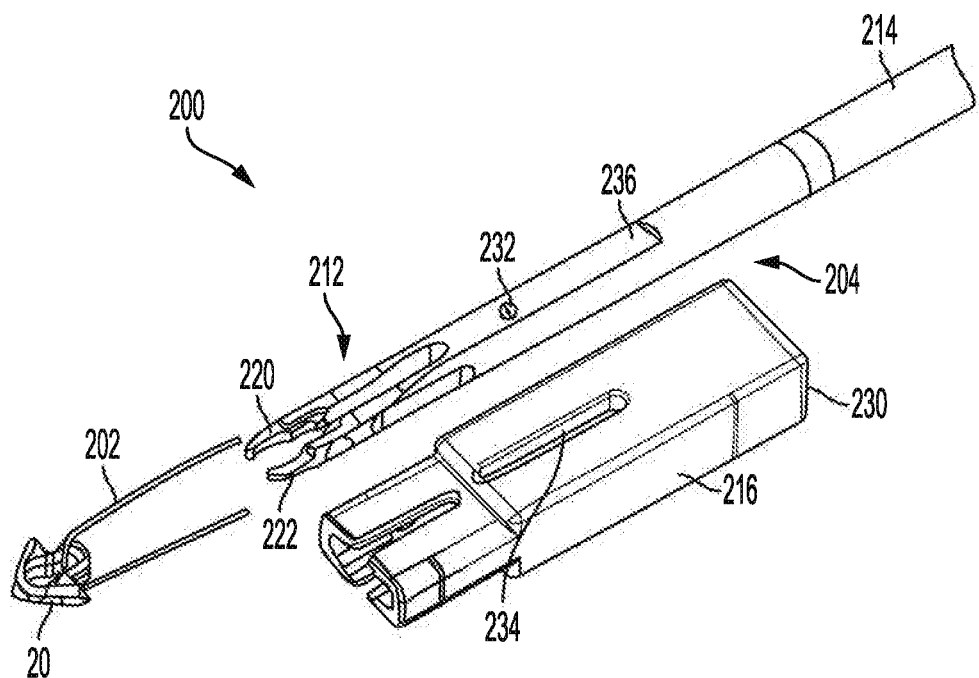
FIG. 9 is and exploded view of the tool illustrating a sleeve removed from a shaft of the tool.

FIG. 9 is exploded view of a portion of the tissue anchor system 200. The tissue anchor system 200 includes the tissue anchor 20, a length of suture 202 coupled to the tissue anchor 20, and the tool 204 provided with the clip 212 that is configured to be attached to the anchor 20, deliver the anchor 20, and be removed from the anchor 20.

The tool 204 is provided with the clip 212 that is adapted to engage with the anchor 20. In one embodiment, the clip 212 includes a first clip arm 220 and a second clip arm 222. The first clip arm 220 is insertable through the slot 60 (FIG. 2) and the second clip arm 222 is insertable into the slot 62. In this way, the clip arms 220, 222 of the clip 212 slide into and engage the entire longitudinal extent of the anchor 20.

The sleeve 216 is retractable and slides relative to the shaft 214 of the tool 204. In one embodiment, the sleeve 216 is assembled to the shaft 214 by sliding the proximal end 230 of the sleeve 216 over the clip 212 and inserting a pin 232 into a gate 234 of the sleeve 216. The pin 232 is permanently connected to the shaft 214 to ensure that both the pin 232 and the sleeve 216 remain coupled to the tool 204 throughout its life cycle. In one embodiment, the pin 232 is provided with a ramp that inclines from the distal end to the proximal end of the pin 232. The ramped pin 232 allow the sleeve 216 to slide up the pin 232 when the sleeve 216 is pushed in a proximal direction to attach the sleeve 216 to the shaft 214. The ramped pin 232 prevents the sleeve 216 from sliding off the shaft 214 in the distal direction. The sleeve 216 is retractable relative to the clip 212 by a retraction distance that is equal to a length of the gate 234 formed in the top surface of the sleeve 216. In one embodiment, the pin 232 and the gate 234 combine to provide the sleeve 216 with a stroke in a range of about 4-12 mm, preferably the stroke of the sleeve 216 along the shaft 214 is in a range of about 6-9 mm.

In one embodiment, the shaft 214 includes a flat 236 that engages with and prevents rotation of the sleeve 216 relative to the shaft 214.

Figure 10:
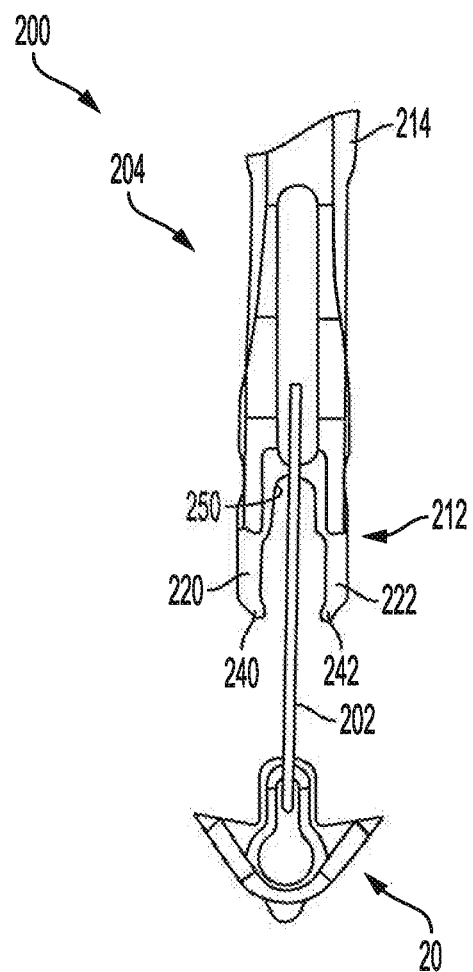
FIG. 10 is a top view of the shaft of the tool.
Figure 11:
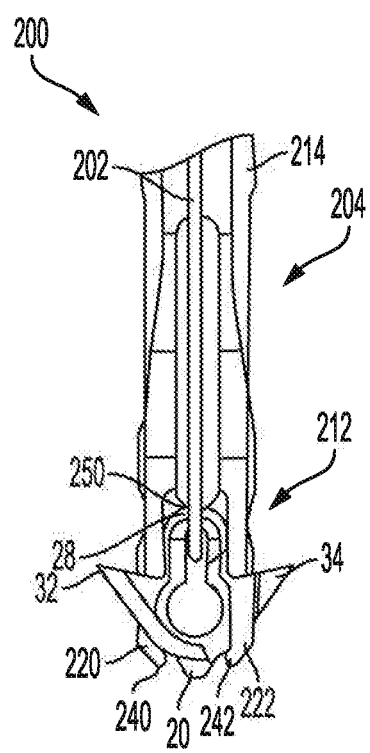
FIG. 11 is a top view of the anchor illustrated in FIG. 1 engaged with the shaft illustrated in FIG. 10.

FIG. 10 is a top view of the clip 212 positioned for engagement with the anchor 20, and FIG. 11 is a top view of the clip 212 coupled to the anchor 20. In one embodiment, a back-table nurse or the surgeon will load the anchor 20 into the tool 204 by maintaining the suture 220 in a comfortable position along the shaft 214 of the tool. The first clip arm to 20 and the second clip arm 222 are inserted into the slots 60, 62, respectively, of the anchor 20. Each of the clip arms 220, 222 extend through an entire longitudinal length of the anchor 20. In one embodiment, the first clip arm 220 includes a first pincher 240 and the second clip arm 222 includes a second pincher 242. The pinchers 240, 242 are flexible and move laterally to allow engagement of the pinchers with the anchor 20. FIG. 11 illustrates the anchor 20 engaged with the clip 212 where the first pincher 240 and the second pincher 242 pinch inwardly to capture the anchor 20 within the clip 212. The shank 28 of the anchor 20 bottoms out and is in contact with a base 250 located between the first clip arm 220 and the second clip arm 222. This allows the tool 204 to push the anchor 20 into soft tissue.

Figure 12:
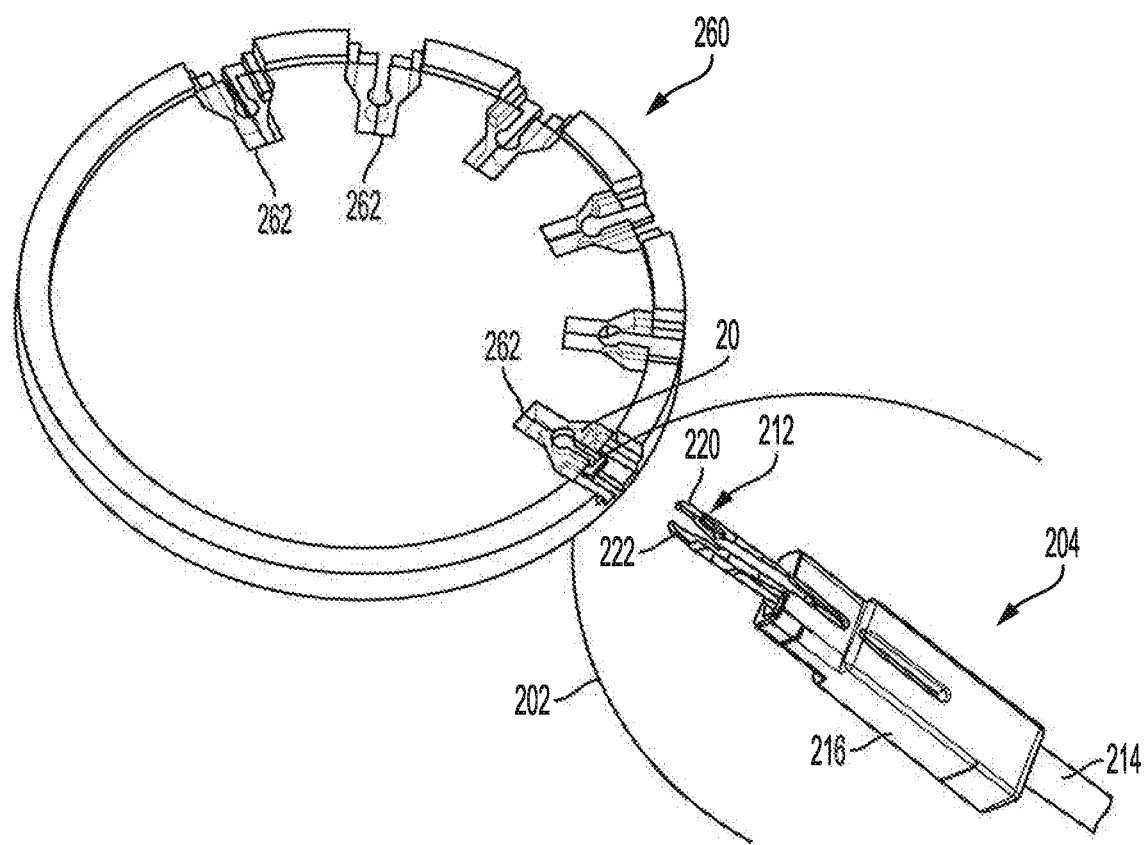
FIG. 12 is a perspective view of one embodiment of a tool position to remove an anchor captured in an anchor cartridge.

FIG. 12 is a perspective view of a cartridge 260 maintaining one or more anchors 20 in position for loading into the tool 204. The anchors 20 are small. The anchors 20 can be manually loaded into the tool 204. The cartridge 260 provides a convenient increased grasping area that allows easy handling of the small anchors 20. In one embodiment, the cartridge 260 holds a plurality of the anchors 20 within individual garages 262. The sleeve 216 is retracted in a proximal direction to expose the clip 212. The clip 212 is inserted into the garage 262 and the first clip arm 220 is inserted into the first slot 60 and the second clip arm 222 is inserted into the second slot 62 of the anchor 20. As illustrated in FIG. 11, the pinchers 240, 242 close upon the anchor 20. The sleeve 216 is moved in a distal direction to close the clip arms 220, 222 into engagement with the anchor 20. In this configuration, the sleeve 216 is disposed over both the clip arms 220, 222 and the anchor 22 protectively prevent snagging the anchor against tissue during the placement procedure of the anchor inside of the body.

FIG. 13A-FIG. 13D illustrate delivery motions of the anchor from the tissue anchor system 200.

FIG. 13A is a top view and FIG. 13B is a sectional view that illustrate the anchor 20 engaged by the clip 212 and protectively covered by the sleeve 216. When the sleeve 216 is in the distalmost position protectively covering the clip 212, the sleeve 216 operates to pinch the clip arms 220, 222 inward to capture the anchor 20. In one embodiment, each of the pinch arms 220, 222 includes an indent 270 and the sleeve includes a detent 272 that pushes against the indent 270 to hold the clip arms 220, 222 against the anchor 20.

FIG. 13C illustrates the sleeve 216 retracted in a proximal direction and out of engagement with the clip arms 220, 222. The clip arms 220, 222 engaged to hold the anchor 20, but also allow the anchor 20 to slide relative to the clip 212. FIG. 13C illustrates embodiment where the shaft 214 has been pushed in a distal direction to engage the anchor 20 with soft tissue.

FIG. 13D illustrates that the anchor 20 has been delivered out from the clip 212 and the sleeve 216 has been moved in the distal direction over the clip 212. In this configuration, the anchor 20 has been delivered and the tool 204 is in position for removal from the patient.

The slideable sheath 216 encloses the clip 212 and the anchor 20 to ensure that these components do not drag or catch soft tissue as the anchor 20 is carried through a surgical dissection to the targeted anchor site. The clip 212 slides within the sheath 216, and the clip arms 220, 222 flex outward when they pass in the distal direction beyond the distal end of the sheath 216. This feature prevents unintentional release of the anchor 20 while the anchor 20 is retracted within the sheath 216. The sheath 216 has the internal detent bumps 270 that mate with indentations 272 on the clip 212, which prevents the sliding motion between the clip 212 and the sheath 216 until enough force is applied to the distal end of the sheath 216. Thus, the anchor 20 will only be exposed when the distal end of the sheath 216 is pressed with sufficient force against the target soft tissue, for example, through application of a thrust force on the clip 212. In one embodiment, a biasing spring is employed in place of the detent 270 to achieve the same resistance to sliding movement.

FIG. 14 is a perspective view of one embodiment of an anchor 20. The tissue anchor 20 includes a distal end 40 opposite of a proximal end 42. In certain instances, the distal end 40 of the anchor 20 is blunt, although the anchor tapers to the distal end to allow for tissue penetration. The anchor 20 includes a central region CR between the distal end 40 and the proximal end 42. In addition, the anchor 20 includes a first barb 32, a second barb 34, and a third barb 36 extending from the central region CR. As shown in FIGS. 16-18, and as explained in further detail below, the first barb 32 and the second barb 32 extend laterally from the central region CR. In certain instances, the third barb 36 extends from the central region CR substantially perpendicular to the first barb 32 and/or the second barb 34.

The central region CR includes a top surface 44, and side surfaces 46, 48 with the first barb 32 and the second barb 34 extending in opposite directions from opposing side surfaces 46, 48 of the central region CR. The opposing side surfaces 46, 48 are laterally opposing surfaces, and the slot 60 is longitudinal relative to the laterally side surfaces 46, 48. In addition, the third barb 36 extends from the top surface 44 of the central region CR. In certain instances, the third barb 36 has a width less than a width of the central region CR.

Figure 19:
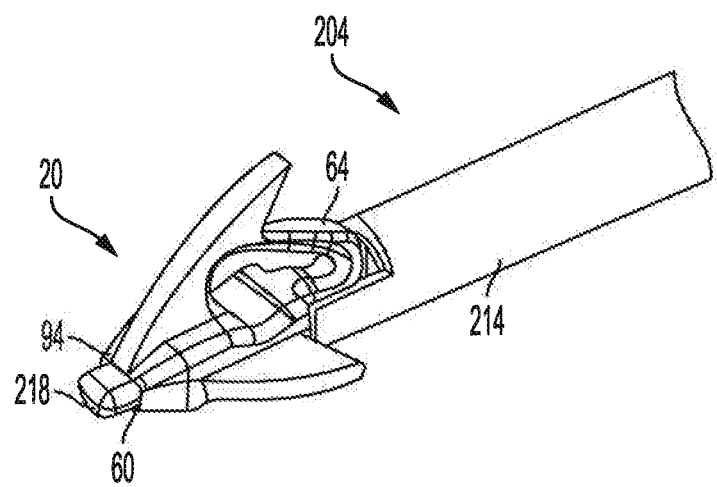
FIG. 19 is a perspective view of a distal end of a tool for placing an anchor in a first configuration.
Figure 20:
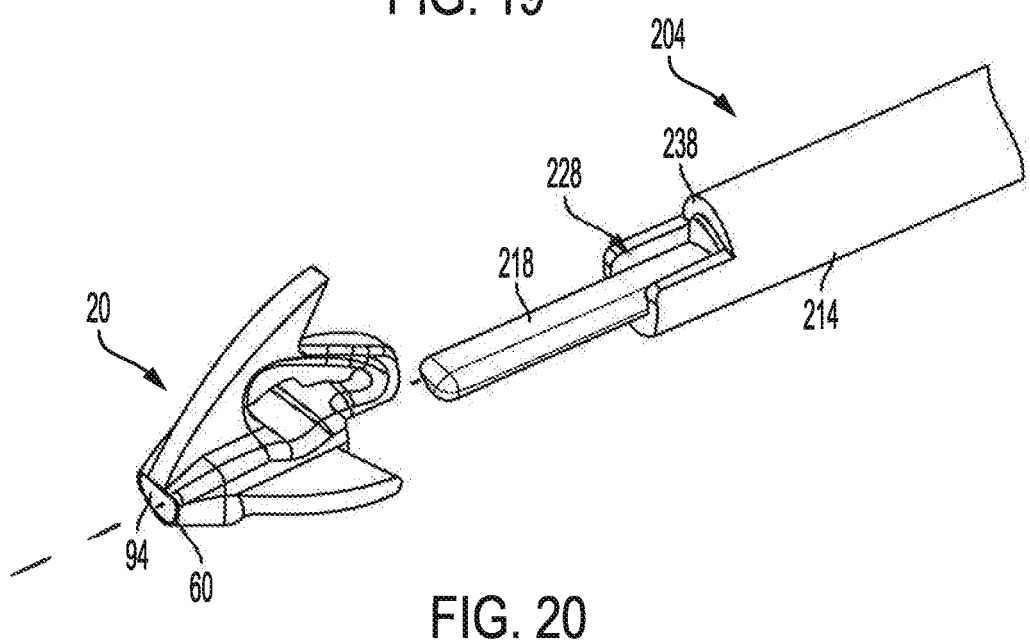
FIG. 20 is a perspective view of the distal end of the tool, illustrated in FIG. 19, in a second configuration.

The anchor 20 also includes a slot 60 arranged through the central region CR from the distal end 40 to the proximal end 42 as is shown in further detail in FIGS. 15-16. The slot 60 is configured to interface with a delivery mechanism as shown in FIGS. 19-20. The slot 60 may be vertically offset from an aperture 54. The aperture 54 allows passage of a suture (e.g., a surgeon's choice of a prepackaged, double-armed suture) as shown in FIG. 15. In certain instances, the anchor 20 includes a proximal portion 64 with the aperture 54 extending laterally through the proximal portion 64. The aperture 54 extends laterally through the anchor 20 and the slot 60 extends axially through the anchor 20.

FIG. 15 is a side view of the anchor 20 and FIG. 16 is a front view of the anchor 20. As shown in FIG. 15, the tissue anchor 20 may be coupled with a double-armed suture 80. The double-armed suture 80 includes a length of suture 82 having a first needle 84 connected to a first end of the suture 82 and a second needle 86 connected to a second end of the suture 82. As shown, the aperture 54 includes a first portion 68 and a second portion 76. The first portion 68 and the second portion 76 of the aperture 54 may be of different sizes. For example, the first portion 68 of the aperture 54 may be smaller than the second portion 76 of the aperture 54. In certain instances, the aperture 54 increases in size toward the distal end 40 of the anchor 20. This arrangement of the aperture 54 facilitates arrangement of the suture 80 through the anchor 20. The anchor 20 provides a large target opening for passing one of the needles 84, 86 through the anchor 20. Consequently, passage of the double-armed suture 80 through the aperture 54 of the anchor 20 may be easier and more convenient than passing a double-armed suture through a conventional eyelet of a conventional anchor.

In certain instances, the proximal portion 64 of the central region CR of the anchor 20 extends distal to a proximal end 88 of the slot 60. In certain instances, at least a portion of the aperture 54 is arranged proximal to the slot 60. The third barb 36 may extend from the opposing end 94 of the slot 60. As noted above, the slot 60 is configured to interface with a delivery mechanism. The proximal end 88 of the slot 60 being longitudinally offset from the aperture 54 facilitates interaction with the delivery tool while allowing the surgeon to thread the suture 80 through the aperture 54. As shown in FIGS. 14, 15, 18, the aperture 54, by way of the proximal portion 64 of the anchor 20, extends longitudinally beyond the third barb 36.

As shown in FIGS. 16-18, and as explained in further detail below, the first barb 32 and the second barb 34 extend laterally from the central region CR. The first barb 32 and the second barb 34 may extend at a downward angle relative to the opposing side surfaces 46, 48 of the central region CR. In certain instances, the opposing side surfaces 46, 48 do not extend vertically below the remaining portions of the central region CR The slot 60 includes an upper surface 90 and a lower surface 92. In certain instances, and as shown in FIG. 16, the upper surface 90 of the slot 60 extends across the central region CR. In addition, the upper surface 90 of the slot 60 is substantially flat. The lower surface 92 of the slot 60 may be curved. In certain instances, the lower surface 92 of the slot 60 is a semi-circle. The non-circular shape of the slot 60 facilitates interaction with a delivery tool. As shown in FIG. 18, the proximal portion 64 of the anchor 20 may have a width greater than a width of the third barb 36.

FIG. 19 is a perspective view of a tool 204 for placing an anchor in a first configuration with the anchor 20 coupled to the tool 204 and FIG. 20 is a perspective view of the tool 204 in a second configuration with the anchor 20 uncoupled from the tool 204. The tool 204 includes a shaft 218 that is configured to extend through the slot 60 in the anchor 20. Slot 60 and shaft 218 may be sized such that there is an interference fit that prevents anchor 20 from easily detaching from tool 204. In certain instances, and as shown in FIG. 19, the shaft 218 extends beyond the distal end 94 of the slot 60.

The anchor 20 may rest within a portion of the tool 204. The tool 204 may include a cannula (or a tube) 214 supporting the shaft 218. As discussed in detail with reference to FIG. 21, the tool 204 may include a mechanism to retract the shaft 218 to cause the cannula 214 to force or push the anchor 20 from the shaft 218.

As shown in comparing FIGS. 19 and 20, the proximal portion 64 of the anchor 20 may nest within the cannula 214. The cannula 214 may include a groove 228 into which the proximal portion 64 of the anchor 20 may nest within when the anchor 20 is coupled to the tool 204. Actuation of the shaft 218 forces the proximal portion 64 of the anchor 20 from the groove 228 by pushing the anchor 20 from an end 238 of the tool 204.

The tool 204 facilitates placement of the anchor 20 into soft tissue such as the sacrospinous ligament or the arcus tendineus ligament. As noted above, the anchor 20 may include a suture 82. In certain instances, two anchors 20 may be embedded in the left and right sacrospinous ligament and two anchors 20 within the left and right arcus tendineus ligament or nearby muscle. The support material 140 may be guided through an incision (e.g., a vaginal incision) and a physician can couple the support material 140 to each one of the sutures 82 that are arranged through the anchors 20. Sutures 82 extending from the anchors 20 may serve as guides for a support material 140 (discussed in detail above). The support material 140 may be slid along the sutures 82.

Figure 21:
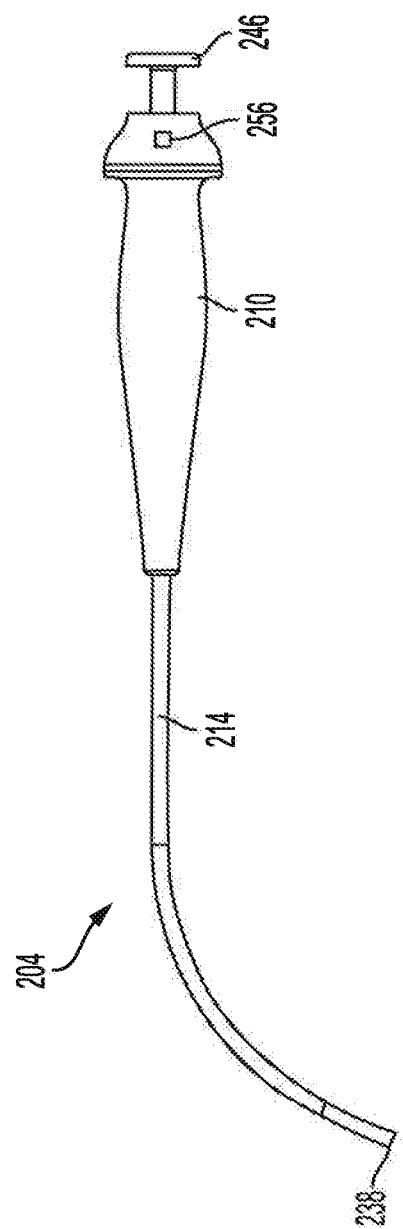
FIG. 21 is a side view of a tool for placing an anchor.

FIG. 21 is a side view of a tool 204 for placing an anchor. The tool 204 includes a handle 210 on a proximal end, a cannula 214 coupled to the handle 210, a cannula (shown in FIGS. 19 and 20), and a plunger button 246. The plunger button 246 is used to actuate the delivery mechanism, causing the shaft 218 and anchor 20 at the distal end 238 to extend into the target tissue. The plunger button 246 may be spring-loaded to minimize unintended actuation.

In certain instances, the plunger button 246 also includes a locking mechanism that engages when the plunger button 246 is actuated beyond a certain point. This provides feedback such that actuation has been fully completed and keeps the shaft 218 extended for subsequent reloading with a subsequent anchor 20 if desired. This locking mechanism will be disengaged by pushing an option button 256, twisting the plunger button 246, or pulling back on the plunger button 246.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein. Therefore, it is intended that this invention be limited only by the claims and the equivalents thereof.

What is claimed is:

1. A tissue anchor comprising:
a leading-most end opposite of a trailing-most end, with a central longitudinal axis oriented from the leading-most end to the trailing-most end, with the leading-most end pointed and configured to penetrate tissue;
a front side opposite of a back side, with each of the front side and the back side of the tissue anchor including a central region centered on the central longitudinal axis, a first lateral region extending from the central region to a first barb, and a second lateral region extending opposite of the first lateral region from the central region to a second barb;
an opening formed entirely through the front side and the back side and the central region of the tissue anchor, with the opening including a first aperture connected to a second aperture, with a diameter of the first aperture larger than a diameter of the second aperture by at least a factor of two, with the opening occupying more than 40% of a total area of the central region;
a first slot formed longitudinally through an entirety of the first lateral region between the front side and the back side of the tissue anchor; and
a second slot formed longitudinally through an entirety of the second lateral region between the front side and the back side of the tissue anchor;
wherein a width of the tissue anchor measured from an end of the first barb across the central region to an end of the second barb is larger than a depth of the tissue anchor measured from the front side to the back side by at least a factor of three.

2. The tissue anchor of claim 1, wherein an entirety of the first aperture is located between the leading-most end and the first barb.

3. The tissue anchor of claim 1, wherein a pointed end of the first barb is located a longitudinal distance from the leading-most end of the tissue anchor, and an entirety of the first aperture is within the longitudinal distance.

4. The tissue anchor of claim 1, wherein a distal portion of the tissue anchor includes the leading-most end and the first barb and the second barb, and a proximal portion of the tissue anchor includes a shank attached to the distal portion, with the second aperture formed in the shank and an entirety of the first aperture is formed in the distal portion of the tissue anchor.

5. The tissue anchor of claim 1, further comprising:
a length of suture inserted into the opening, and a needle connected to the length of suture;
wherein the diameter of the first aperture is at least 3 times larger than a diameter of the needle.

6. The tissue anchor of claim 1, wherein each of the front side and the back side of the tissue anchor being bi-laterally symmetric relative to the central longitudinal axis.

7. The tissue anchor of claim 1, wherein each of the first slot and the second slot are parallel with the central longitudinal axis.

8. The tissue anchor of claim 1, wherein, when viewed from the leading-most end along the central longitudinal axis, the first slot is a first rectangular opening formed in the first lateral region and the second slot is a second rectangular opening formed in the second lateral region.

9. The tissue anchor of claim 8, wherein the first rectangular opening and the second rectangular opening combine to occupy about 20 percent of a total frontal area of the tissue anchor.

10. The tissue anchor of claim 1, wherein the opening is separated from the first slot and the second slot by a wall.

11. The tissue anchor of claim 1, further comprising:
a length of suture looped through the opening of the tissue anchor and having a first suture section extending away from the front side of the tissue anchor and a second suture section extending away from the back side of the tissue anchor; and
an adjustable anchor coupled to the length of suture, with the adjustable anchor including a sleeve placed over a central shaft, with the sleeve having a single proximal hole formed through the sleeve, a first distal hole formed through the sleeve, and a second distal hole formed through the sleeve, with the single proximal hole located between opposing lateral edges of the sleeve and placed laterally between the first distal hole and the second distal hole;
wherein the first suture section and the second suture section are each inserted into the single proximal hole formed in the sleeve and retained between the sleeve and the central shaft, with the first suture section exiting the sleeve through the first distal hole and the second suture section exiting the sleeve through the second distal hole.

12. A tissue anchor comprising:
a leading-most end opposite of a trailing-most end, with a central longitudinal axis oriented from the leading-most end to the trailing-most end, with the leading-most end pointed and configured to penetrate tissue;
a front side opposite of a back side, with each of the front side and the back side of the tissue anchor including a central region centered on the central longitudinal axis, a first lateral region extending from the central region to a first barb, and a second lateral region extending opposite of the first lateral region from the central region to a second barb;
an opening formed entirely through the front side and the back side and the central region of the tissue anchor, with the opening including a first aperture connected to a second aperture, with a diameter of the first aperture larger than a diameter of the second aperture by at least a factor of two, with the opening occupying more than 40% of a total area of the central region;
a first slot formed longitudinally through an entirety of the first lateral region between the front side and the back side of the tissue anchor; and
a second slot formed longitudinally through an entirety of the second lateral region between the front side and the back side of the tissue anchor;
wherein a distal portion of the tissue anchor includes the leading-most end and the first barb and the second barb, and a proximal portion of the tissue anchor includes a shank attached to the distal portion, with the second aperture formed in the shank and an entirety of the first aperture is formed in the distal portion of the tissue anchor.

13. A tissue anchor comprising:
a leading-most end opposite of a trailing-most end, with a central longitudinal axis oriented from the leading-most end to the trailing-most end, with the leading-most end pointed and configured to penetrate tissue;
a front side opposite of a back side, with each of the front side and the back side of the tissue anchor including a central region centered on the central longitudinal axis, a first lateral region extending from the central region to a first barb, and a second lateral region extending opposite of the first lateral region from the central region to a second barb;
an opening formed entirely through the front side and the back side and the central region of the tissue anchor, with the opening including a first aperture connected to a second aperture, with a diameter of the first aperture larger than a diameter of the second aperture by at least a factor of two, with the opening occupying more than 40% of a total area of the central region;
a first slot formed longitudinally through an entirety of the first lateral region between the front side and the back side of the tissue anchor; and
a second slot formed longitudinally through an entirety of the second lateral region between the front side and the back side of the tissue anchor;
wherein, when viewed from the leading-most end along the central longitudinal axis, the first slot is a first rectangular opening formed in the first lateral region and the second slot is a second rectangular opening formed in the second lateral region.

* * * * *

UNITED STATES PATENT AND TRADEMARK OFFICE
CERTIFICATE OF CORRECTION

PATENT NO. : 11,045,184 B2
APPLICATION NO. : 16/296293
DATED : June 29, 2021
INVENTOR(S) : John J. Allen It is certified that error appears in the above-identified patent and that said Letters Patent is hereby corrected as shown below:

In the Specification

In Column 5, Line 60, delete "as" and insert -- is --, therefor.

In Column 6, Line 4, delete "and" and insert -- an --, therefor.

In Column 6, Line 12, delete "as" and insert -- is --, therefor.

In Column 6, Line 17, delete "as" and insert -- is --, therefor.

In Column 6, Line 19, delete "as" and insert -- is --, therefor.

In Column 7, Lines 16-17, delete "back side 40" and insert -- backside 42 --, therefor.

In Column 7, Line 41, delete "D to of" and insert -- D2 of --, therefor.

In Column 8, Lines 13-14, delete "first aperture 50" and insert -- first aperture 52 --, therefor.

In Column 9, Line 21, delete "double-armed suture 82" and insert -- double-armed suture 80 --, therefor.

In Column 10, Line 31, delete "of 1.5" and insert -- 1.5 --, therefor.

In Column 10, Line 40, delete "as" and insert -- is --, therefor.

In Column 11, Line 9, delete "tissue anchor 22" and insert -- tissue anchor 20 --, therefor.

In Column 11, Line 49, delete "is" and insert -- is an --, therefor.

In Column 12, Line 24, delete "suture 220" and insert -- suture 202 --, therefor.

Signed and Sealed this
Twenty-seventh Day of September, 2022

Katherine Kelly Vidal
*Director of the United States Patent and Trademark Office*

In Column 12, Lines 25-26, delete "first clip arm to 20" and insert -- first clip arm 220 --, therefor.

In Column 12, Line 56, delete "anchor 22" and insert -- anchor 20 --, therefor.

In Column 12, Line 67, delete "pinch arms 220, 222" and insert -- clip arms 220, 222 --, therefor.

In Column 13, Line 45, delete "second barb 32" and insert -- second barb 34 --, therefor.

In Column 14, Line 16, delete "suture 80" and insert -- suture 82 --, therefor.

In Column 14, Line 32, delete "suture 80" and insert -- suture 82 --, therefor.